United States Patent
Baek et al.

(10) Patent No.: US 10,160,770 B2
(45) Date of Patent: *Dec. 25, 2018

(54) METHOD FOR PREPARING THIENOPYRIMIDINE COMPOUND AND INTERMEDIATES USED THEREIN

(71) Applicant: HANMI PHARM. CO., LTD., Hwaseong-si, Gyeonggi-do (KR)

(72) Inventors: Jong Ouk Baek, Seoul (KR); Jae Hyuk Jung, Seoul (KR); Ho Seok Kim, Jeonju-si (KR); Tae Hee Ha, Hwaseong-si (KR); Kwee Hyun Suh, Suwon-si (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/025,784

(22) Filed: Jul. 2, 2018

(65) Prior Publication Data

US 2018/0312521 A1    Nov. 1, 2018

Related U.S. Application Data

(62) Division of application No. 15/540,757, filed as application No. PCT/KR2015/014491 on Dec. 30, 2015, now Pat. No. 10,040,801.

(30) Foreign Application Priority Data

Dec. 30, 2014    (KR) ........................ 10-2014-0192918

(51) Int. Cl.
*C07D 495/04*    (2006.01)
*A61K 31/519*    (2006.01)

(52) U.S. Cl.
CPC .................................. *C07D 495/04* (2013.01)

(58) Field of Classification Search
CPC ........................... C07D 495/04; A61K 31/519
See application file for complete search history.

(56) References Cited

U.S. PATENT DOCUMENTS

| 6,245,759 | B1 | 6/2001 | Bilodeau et al. |
| 8,957,065 | B2 | 2/2015 | Cha et al. |
| 2012/0065233 | A1 | 3/2012 | Gregor |
| 2013/0116213 | A1 | 5/2013 | Cha et al. |

FOREIGN PATENT DOCUMENTS

| KR | 10-2011-0139653 A | 12/2011 |
| WO | 2011162515 A2 | 12/2011 |

OTHER PUBLICATIONS

Manisha S. Phoujdar et al., "Microwave-based synthesis of novel thienopyrimidine bioisosteres of gefitinib," Tetrahedron Letter, 2008, pp. 1269-1273, vol. 49.
Yusuke Endo et al., "Discovery and SAR study of 2-(4-pyridylamino)thieno[3,2-d] pyrimidin-4(3H)-ones as soluble and highly potent PDE7 inhibitors," Bioorganic & Medicinal Chemistry Letters, 2015, pp. 649-653, vol. 25.
Written Opinion of the International Searching Authority of PCT/KR2015/014491 dated Jun. 16, 2016.
International Search Report of PCT/KR2015/014491 dated Jun. 16, 2016.

*Primary Examiner* — Susanna Moore
(74) *Attorney, Agent, or Firm* — Sughrue Mion, PLLC

(57) ABSTRACT

A method for preparing a thienopyrimidine compound of Formula 1, which is a selective inhibitor of tyrosine kinase activity, in particular, of mutant epidermal growth factor receptor tyrosine kinase. Intermediates used in the method are provided.

4 Claims, No Drawings

METHOD FOR PREPARING THIENOPYRIMIDINE COMPOUND AND INTERMEDIATES USED THEREIN

CROSS REFERENCE TO RELATED APPLICATIONS

This application is a Divisional Application of U.S. application Ser. No. 15/540,757, filed Jun. 29, 2017 in the U.S. Patent and Trademark Office, which is a National Stage of International Application No. PCT/KR2015/014491 filed Dec. 30, 2015, claiming priority based on Korean Patent Application No. 10-2014-0192918 filed Dec. 30, 2014, the contents of all of which are incorporated herein by reference in their entirety.

TECHNICAL FIELD

The present invention relates to a novel method for preparing thienopyrimidine compound having an activity of selectively inhibiting tyrosine kinase, specifically the mutant epidermal growth factor receptor tyrosine kinase; and novel intermediates used therein.

BACKGROUND ART

U.S. Pat. No. 8,957,065 and International Publication No. WO 2011/162515 disclose a thienopyrimidine compound having an activity of selectively inhibiting the mutant epidermal growth factor receptor tyrosine kinase, represented by the following Formula 1.

[Formula 1]

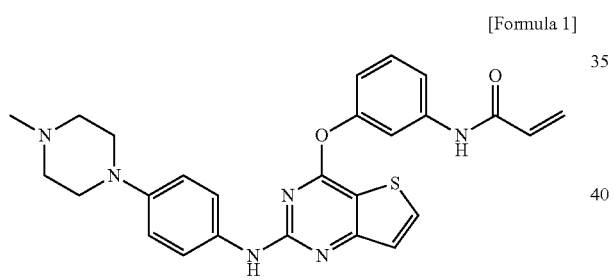

Also, the above documents disclose a method for preparing the compound of Formula 1. Specifically, as illustrated in Scheme 1 below, the method comprises reacting 2,4-dichlorothieno[3,2-d]pyrimidine of Formula 5A with 3-nitrophenol to prepare the compound of Formula A; reacting the compound of Formula A with 4-(4-methylpiperazin-1-yl)aniline to prepare the compound of Formula B; then reducing the nitro group of the compound of Formula B to prepare the compound of Formula C; and reacting the compound of Formula C with acryloyl chloride to prepare the compound of Formula 1.

[Scheme 1]

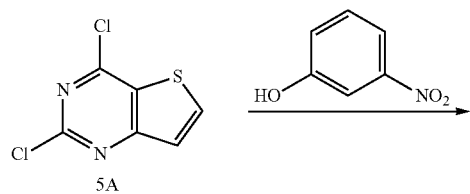

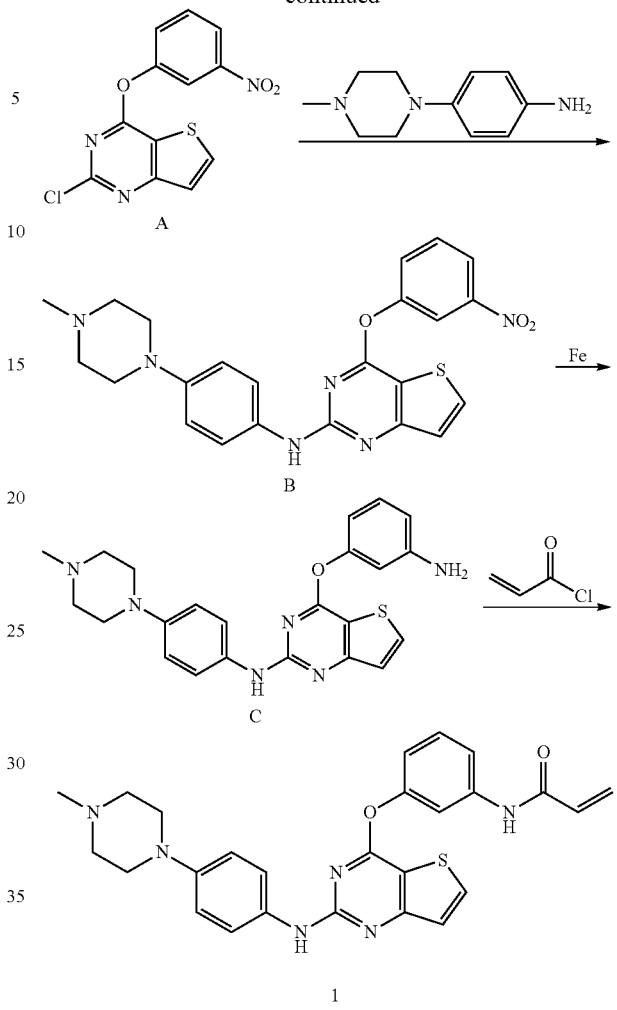

However, the synthesis of the compound in accordance with Scheme 1 has several problems, as explained below. In order to remove impurities generated in the step of obtaining the compound of Formula B, a column chromatography purification method was used, but the method is not suitable for industrial production, giving a low yield. Further, an excess amount of iron is required for reducing the nitro group of the compound of Formula B, and the compound of Formula C thus obtained is reacted with acryloyl chloride, which is hard to handle. In addition, the compounds of Formula C and Formula 1 both need to be purified by using a column chromatography, which is difficult to apply to the industrial production.

Thus, the present inventors have accomplished the present invention by developing a novel method for preparing a selective inhibitor of tyrosine kinase activity, which is convenient and has a high selectivity of reaction.

PRIOR-ART DOCUMENTS

Patent Documents

Patent Document 1: U.S. Pat. No. 8,957,065
Patent Document 2: International Publication No. WO 2011/162515

DISCLOSURE

Technical Problem

An object of the present invention is to provide a method for effectively preparing a thienopyrimidine compound in high yield and purity.

Another object of the present invention is to provide intermediates used in the method for preparing the thienopyrimidine compound.

Still another object of the present invention is to provide a method for preparing the intermediates.

Technical Solution

To solve the problems, the present invention provides a method for preparing a compound of Formula 1, which comprises the steps of:

a. allowing a compound of Formula 3 or a salt thereof to react with a chlorinating agent, preferably in the presence of an organic solvent, to obtain a compound of Formula 2 or a salt thereof; and b. allowing the compound of Formula 2 or the salt thereof to react with a compound of Formula 8 or a salt thereof and a base, preferably in the presence of an organic solvent:

[Formula 1]

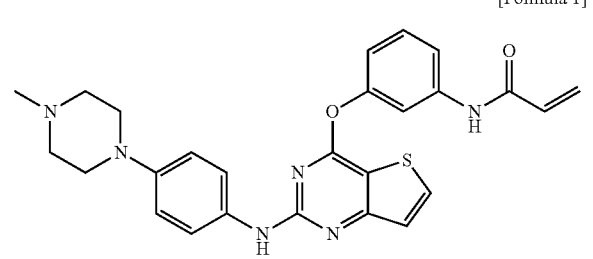

[Formula 2]

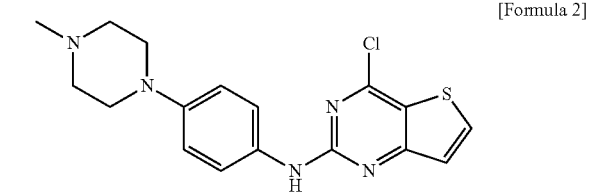

[Formula 3]

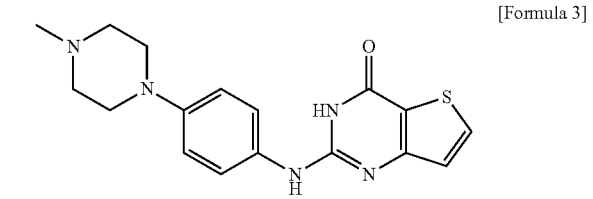

[Formula 8]

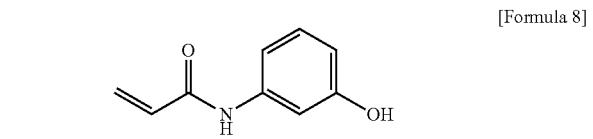

To solve the problems, the present invention also provides a compound of Formula 2 or a salt thereof:

[Formula 2]

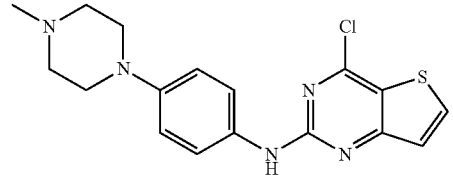

To solve the problems, the present invention also provides a compound of Formula 3 or a salt thereof:

[Formula 3]

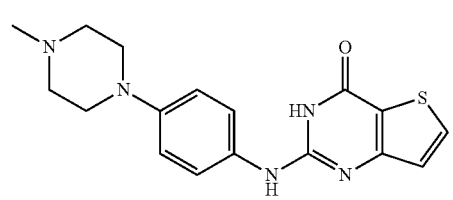

To solve the problems, the present invention also provides a compound of Formula 4 or a salt thereof:

[Formula 4]

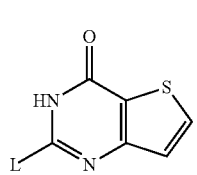

In Formula 4, L is halogen or

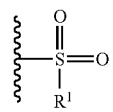

and $R^1$ is $C_{1-10}$ alkyl or benzyl. More specifically, L is

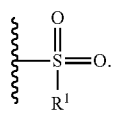

To solve the problems, the present invention also provides a compound of Formula 6 or a salt thereof:

[Formula 6]

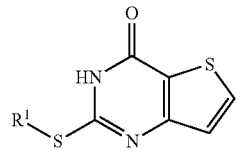

In Formula 6, $R^1$ is $C_{1-10}$ alkyl or benzyl.

To solve the problems, the present invention also provides a method for preparing a compound of Formula 3 or a salt thereof, comprising the step of allowing a compound of Formula 4 or a salt thereof to react with a compound of Formula 9 or a salt thereof and an organic acid, preferably in the presence of an organic solvent:

a. allowing a compound of Formula 3 or a salt thereof to react with a chlorinating agent, preferably in the presence of an organic solvent, to obtain a compound of Formula 2 or a salt therof; and b. allowing the compound of Formula 2 or the salt thereof to react with a compound of Formula 8 or a salt thereof and a base, preferably in the presence of an organic solvent:

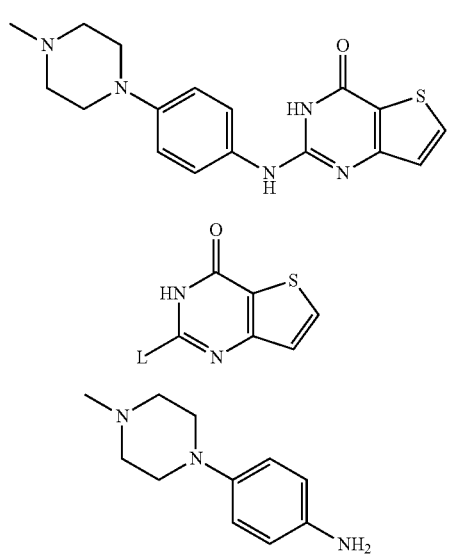

[Formula 3]

[Formula 4]

[Formula 9]

In Formula 4, L is

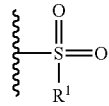

or halogen and R¹ is $C_{1-10}$ alkyl or benzyl.

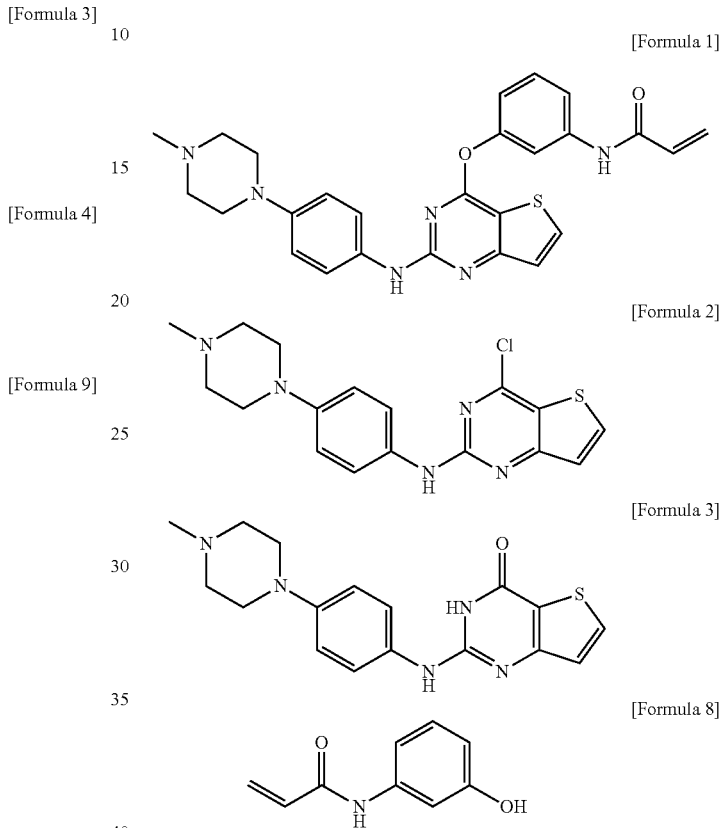

[Formula 1]

[Formula 2]

[Formula 3]

[Formula 8]

Advantageous Effects

Using the method of the present invention, the industrial mass-production of the compound of Formula 1, which is useful as a therapeutic agent for cancer induced by the mutant epidermal growth factor receptor tyrosine kinase, can be implemented more conveniently and efficiently than the conventional technology.

BEST MODE

Hereinafter, the present invention will be described in detail.

The term "halogen" as used herein encompasses fluorine, chlorine, bromine and iodine, preferred are chlorine, bromine and iodine, especially preferred is chlorine.

Unless specifically stated otherwise, the term "alkyl" as used herein refers to a linear or branched hydrocarbon residue, and examples of the alkyl may include methyl, ethyl, propyl, butyl, and the like.

The chemical structure of a compound of Formula 3, 4, 6 or 7 represented in a keto form herein may also be indicated in an enol form.

The present invention provides a method for preparing a compound of Formula 1, comprising the steps of:

Preparation of Compound of Formula 2 Using Compound of Formula 3 as Starting Material The present invention provides a step a. allowing a compound of Formula 3 or a salt thereof to react with a chlorinating agent in the presence of an organic solvent to obtain a compound of Formula 2 or a salt thereof.

In the process for preparing the compound of Formula 2, the organic solvent used in the reaction may be selected from the group consisting of acetonitrile, dichloromethane, chloroform, dioxane, N'N'-dimethyl formamide, N'N-dimethyl acetamide, and a mixture thereof. According to one embodiment of the present invention, the organic solvent may be acetonitrile. The organic solvent may be used in an amount of 1 to 10 mL, specifically 2 to 7 mL, more specifically 3 to 5 mL, based on 1 g of the compound of Formula 3.

The chlorinating agent, which may be used in the reaction, may be selected from the group consisting of phosphorus oxychloride ($POCl_3$), phosphorus trichloride ($PCl_3$), phosphorus pentachloride ($PCl_5$), phosgene ($COCl_2$), diphosgene ($ClCO_2CCl_3$), triphosgene ($Cl_3CCO_2CCl_3$), chlorine ($Cl_2$), oxalyl chloride (($COCl)_2$), thionyl chloride ($SOCl_2$), sulfuryl chloride ($SO_2Cl_2$), and a mixture thereof. According to one embodiment of the present invention, the chlorinating agent may be phosphorus oxychloride ($POCl_3$). The chlorinating agent may be used in an amount of 1.0 to 5.0 mole equivalents, specifically 2.0 to 4.0 mole equivalents, based on 1 mole equivalent of the compound of Formula 3.

The phosphorus oxychloride may be mixed with the above-mentioned organic solvent to be added to the reaction solution. The mixed solvent may be used as a mixture of acetonitrile and phosphorus oxychloride in a volumetric ratio of 10:1 to 1:1, specifically 5:1 to 3:1. According to one embodiment of the present invention, the compound of Formula 3 may be dissolved in acetonitrile solvent first, and a mixture of acetonitrile and phosphorus oxychloride in a volumetric ratio of 1:1 to 2:1 may be added thereto.

The reaction may be performed under stirring at 50 to 100° C., specifically 60 to 90° C., more specifically 70 to 80° C. for 10 minutes to 10 hours, specifically 0.5 to 5 hours, more specifically 1 to 2 hours.

The compound of Formula 2 may be obtained in a solid form by adding aqueous sodium hydroxide solution to the reaction solution of organic solvent at 5 to 25° C., specifically 10 to 20° C., to precipitate the compound of Formula 2.

According to the present invention, the process for preparing the compound of Formula 2 may further include the steps of dissolving the compound of Formula 2 obtained in the previous step in an organic solvent once again, followed by distillation under reduced pressure and crystallization with an organic solvent or a water-miscible organic solvent to raise the purity.

In the step of raising the purity of the compound of Formula 2, the organic solvent used for dissolving the compound of Formula 2 may be selected from the group consisting of dichloromethane, chloroform, ethyl acetate, acetone, acetonitrile, methanol, ethanol, isopropanol, and a mixture thereof. According to one embodiment of the present invention, the organic solvent may be a mixture of dichloromethane and methanol, and the mixing ratio may be 1:1 to 5:1, specifically 1:1 to 2:1 in a volumetric ratio. The reaction using the mixed solvent may be performed under stirring at 10 to 50° C., specifically 15 to 40° C., more specifically 20 to 30° C. for 1 to 10 hours, specifically 1 to 5 hours, more specifically 1 to 2 hours.

In the step of raising the purity of the compound of Formula 2, the organic solvent or water-miscible organic solvent used for crystallization of the compound of Formula 2 after distillation under reduced pressure may be selected from the group consisting of acetone, acetonitrile, methanol, ethanol, isopropanol, and a mixture thereof with water. According to one embodiment of the present invention, the organic solvent may be a mixture of acetone and water, and the mixing ratio may be 10:1 to 1:1, specifically 6:1 to 3:1 in a volumetric ratio. The crystallization using the mixed solvent may be performed under stirring at 10 to 50° C., specifically 15 to 40° C., more specifically 20 to 30° C. for 1 to 10 hours, specifically 1 to 5 hours, more specifically 1 to 2 hours.

Preparation of Compound of Formula 1 Using Compound of Formula 2 as Starting Material The present invention provides a step b. allowing the compound of Formula 2 (obtained as described above) or a salt thereof to react with a compound of Formula 8 or a salt thereof and a base, preferably in the presence of an organic solvent, to obtain a compound of Formula 1.

In the process for preparing the compound of Formula 1, the compound of Formula 8 or the salt thereof which is reacted with the compound of Formula 2 or the salt thereof may be used in an amount of 1.0 to 2.0 mole equivalents, specifically 1.1 to 1.5 mole equivalents, more specifically 1.2 to 1.3 mole equivalents, based on 1 mole equivalent of the compound of Formula 2.

The process for preparing the compound of Formula 1 may be performed in the presence of an organic solvent. The organic solvent may be selected from the group consisting of acetonitrile, acetone, methyl ethyl ketone, methyl isobutyl ketone, methyl acetate, ethyl acetate, isopropyl acetate, N'N'-dimethyl formamide, N'N-dimethyl acetamide, dimethyl sulfoxide, and a mixture thereof. According to one embodiment of the present invention, the organic solvent may be acetonitrile. The organic acid may be used in an amount of 5 to 20 mL, specifically 7 to 15 mL, more specifically 8 to 12 mL, based on 1 g of the compound of Formula 2. The reaction may be performed at a reflux temperature of solvent for 1 to 10 hours, specifically 3 to 8 hours, more specifically 5 to 7 hours.

The base used in the above reaction may be potassium carbonate, sodium carbonate, potassium hydroxide, sodium hydroxide, sodium hydrogen carbonate or a mixture thereof. According to one embodiment of the present invention, the base may be potassium carbonate or sodium carbonate. The base may be used in an amount of 1.0 to 5.0 mole equivalents, specifically 2.5 to 3.5 mole equivalents, based on 1 mole equivalent of the compound of Formula 2. According to one embodiment of the present invention, the base may be used in an amount of 3.0 mole equivalents.

The compound of Formula 1 may be obtained in a solid form by adding water to the reaction solution at 30° C. or lower, specifically at 30 to 20° C., to precipitate the compound of Formula 1. The water may be added in an amount of 10 to 30 mL, specifically 15 to 25 mL, based on 1 g of the compound of Formula 2.

In the above process (and also independent from the overall process), the compound of Formula 3 or the salt thereof may be obtained by a step c. allowing a compound of Formula 4 or a salt thereof to react with a compound of Formula 9 or a salt thereof and an organic acid, preferably in the presence of an organic solvent:

[Formula 4]

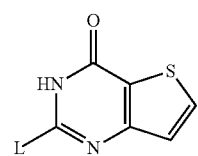

[Formula 9]

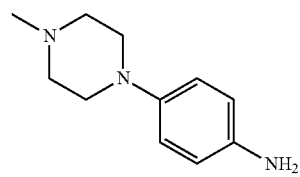

In Formula 4, L is

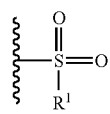

or halogen and $R^1$ is $C_{1-10}$ alkyl or benzyl.

In the compound of Formula 4, L is a leaving group and may be

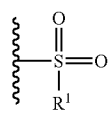

or halogen and $R^1$ is $C_{1-10}$ alkyl or benzyl, and halogen is bromine, chlorine or iodine. Specifically, L may be methanesulfonyl (when $R^1$ is methyl) or chlorine. In a more specific embodiment L is chlorine. Specifically, the compound of Formula 4 may be a compound of Formula 4A or Formula 4B:

[Formula 4A]

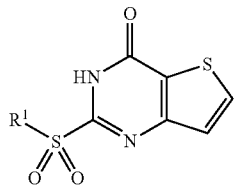

[Formula 4B]

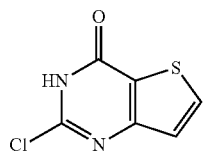

In Formula 4A, $R^1$ is $C_{1-10}$ alkyl or benzyl. In a specific embodiment $R^1$ is methyl.

In the method for preparing a compound of Formula 3, the compound of Formula 9 reacting with the compound of Formula 4 may be used in an amount of 1.0 to 2.0 mole equivalents, specifically 1.2 to 1.5 mole equivalents, based on 1 mole equivalent of the compound of Formula 4.

Also, the organic acid used in the reaction may be acetic acid, trifluoroacetic acid or a mixture thereof, and may be used as an amount of 2.0 to 5.0 mole equivalents, specifically 2.5 to 3.0 mole equivalents, based on 1 mole equivalent of the compound of Formula 4.

The reaction may be performed in a solvent selected from the group consisting of acetonitrile, dimethylformamide, methanol, ethanol, butanol, 2-butanol, isopropanol, and a mixture thereof. In this case, the reaction may be performed under heating reflux conditions at 60 to 100° C., specifically 80° C. for 3 to 20 hours, specifically 6 to 18 hours.

A desired compound of Formula 3 may be obtained from the resulting reaction mixture through either method of the followings:

The desired compound may be obtained in a solid form by an extraction method comprising: cooling the resulting reaction mixture to room temperature, neutralizing it using $NaHCO_3$, extracting the neutralized mixture with dichloromethane, and then allowing the extract to distillation under reduced pressure, followed by crystallization with ethyl acetate.

Alternatively, the desired compound may be obtained in a solid form by a crystallization method comprising: neutralizing the resulting reaction mixture using a base such as sodium hydroxide, potassium hydroxide and triethylamine, and cooling the neutralized mixture to 10 to 30° C.

In the above process (and also independent from the overall process) the compound of Formula 4 or a salt thereof, where L is

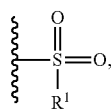

may be obtained by the steps of d. allowing a compound of Formula 7 or a salt thereof to react with an alkylating agent and a base, preferably in the presence of an organic solvent, to obtain a compound of Formula 6 or a salt thereof; and e. allowing the compound of Formula 6 or the salt thereof to react with an oxidizing agent, preferably in the presence of an organic solvent:

[Formula 6]

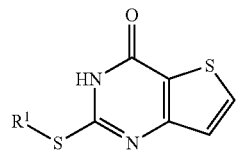

[Formula 7]

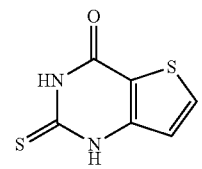

In Formula 6, $R^1$ is $C_{1-10}$ alkyl or benzyl. In a specific embodiment $R^1$ is methyl.

In Step d., the compound of Formula 7 or a salt thereof is allowed to react with an alkylating agent and a base, preferably in the presence of an organic solvent, to obtain the compound of Formula 6 or a salt thereof. The compound of Formula 7 may be prepared using the method disclosed in Korean Laid-open Patent Publication No. 2014-0131943 or is commercially available.

The base in Step d. may be sodium hydroxide, potassium hydroxide, or a mixture thereof, and may be used in an amount of 1.5 to 3.0 mole equivalents, specifically 2.0 to 2.5 mole equivalents, based on 1 mole equivalent of the compound of Formula 7.

The reaction in Step d. may be performed in an organic solvent selected from the group consisting of acetonitrile, methanol, ethanol, butanol, 2-butanol, isopropanol, and a mixture thereof with water. Specifically, the solvent may be a mixed solvent of water and ethanol with the volume ratio of 1:9 to 9:1, more specifically 1:1. The organic solvent may be used in an amount of 5 to 20 mL, specifically 3 to 5 mL, based on 1 g of the compound of Formula 7.

Also, the alkylating agent used in the alkylation reaction may be $R^1$-$R^2$ or $R^1$—O—$S(O)_2$—O—$R^1$, where $R^1$ is $C_{1-10}$ alkyl or benzyl, and $R^2$ is halogen. Specific examples of the alkylating agent may include dimethyl sulfate, methyl iodide, ethyl iodide, benzyl bromide, benzyl chloride, dialkyl sulfate and a mixture thereof, more specifically dimethyl sulfate may be used alone, or a mixture of methyl iodide and dimethyl sulfate. The alkylating agent may be used in an amount of 1.0 mole to 1.4 moles.

The reaction in Step d. may be performed at 15 to 30° C., specifically room temperature for 2 to 6 hours, specifically 3 to 4 hours. Thereafter, the organic solvent distillate under reduced pressure, then the reaction solution may be adjusted to pH 2.0 to 3.5 using concentrated hydrochloric acid, cooled to 5 to 10° C., and then filtered to obtain the compound of Formula 6.

In Step e., the compound of Formula 6 is allowed to react with an oxidizing agent to obtain the compound of Formula 4.

The oxidizing agent in Step e. may be selected from the group consisting of hydrogen peroxide, meta-chloroperoxybenzoic acid, peroxyacetic acid, magnesium monoperoxyphthalate and potassium monosulfate (for example oxone). Specifically, meta-chloroperoxybenzoic acid may be used.

As the oxidizing agent, meta-chloroperoxybenzoic acid (mCPBA) may be used at an amount of 2.0 to 5.0 mole equivalents, specifically 2.5 to 3.0 mole equivalents, based on 1 mole equivalent of the compound of Formula 6.

The reaction in Step e. may be performed in an organic solvent selected from the group consisting of dichloromethane, acetonitrile, methylethyl ketone, methyl isobutyl ketone, methyl acetate, ethyl acetate, isopropyl acetate, diethyl ether, and a mixture thereof. Specifically, methyl acetate or ethyl acetate may be used. The organic solvent may be used in an amount of 5 to 15 mL, specifically 7 to 10 mL, based on 1 g of the compound of Formula 6. The reaction may be performed at 15 to 30° C., specifically room temperature for 2 to 6 hours, specifically 3 to 4 hours, and a solid product in the reaction solution may be filtered to obtain the compound of Formula 4.

In the above process (and also independent from the overall process) the compound of Formula 4 or a salt thereof, where L is halogen, may be obtained by the step of f. hydrolyzing a compound of Formula 5 or a salt thereof in the presence of a base:

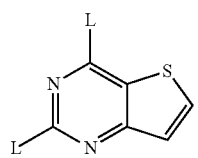

[Formula 5]

In Formula 5, L is halogen.

Specifically, the compound of Formula 5 may be a compound of Formula 5A.

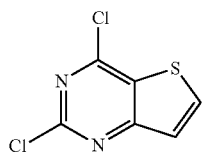

[Formula 5A]

In the hydrolyzing step, the base may be sodium hydroxide, potassium hydroxide, or a mixture thereof, and may be used in an amount of 1.5 to 3.0 mole equivalents, specifically 2.0 to 2.5 mole equivalents, based on 1 mole equivalent of the compound of Formula 5.

The reaction may be performed in an organic solvent selected from the group consisting of tetrahydrofuran, dioxane, acetonitrile, methanol, ethanol, butanol, 2-butanol, isopropanol, and a mixture thereof with water. Specifically, the solvent may be a mixture of the organic solvent and water with the volumetric ratio of 1:9 to 9:1, more specifically 5:1 to 3:1. The solvent may be used in an amount of 5 to 15 mL, based on 1 g of the compound of Formula 5. The reaction may be performed at 20 to 80° C., specifically 30 to 60° C. for 3 to 5 hours. After the reaction temperature is lowered to room temperature, 1.5 to 2.0 equivalents of acetic acid may be added dropwise to the reaction solution to adjust to pH 4 to 6, thereby to obtain a solid compound.

Also, the present invention provides a compound of Formula 2 or a salt thereof useful as an intermediate used to prepare the compound of Formula 1:

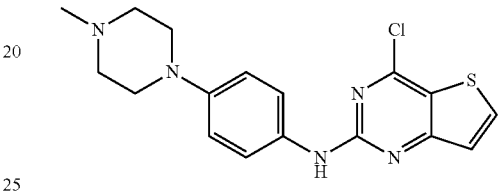

[Formula 2]

Also, the present invention provides a compound of Formula 3 or a salt thereof useful as an intermediate used to prepare the compound of Formula 1:

[Formula 3]

Also, the present invention provides a compound of Formula 4 or a salt thereof useful as an intermediate used to prepare the compound of Formula 1:

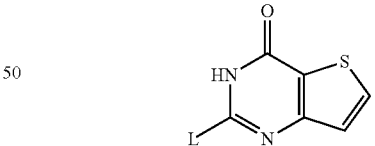

[Formula 4]

In Formula 4, L is

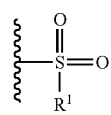

or halogen and $R^1$ is $C_{1-10}$ alkyl or benzyl.

In one embodiment of the present invention, the compound of Formula 4 may be a compound of Formula 4A or a salt thereof or of Formula 4B or a salt thereof:

[Formula 4A]

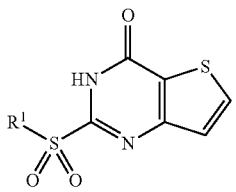

In Formula 4A, $R^1$ is $C_{1-10}$ alkyl or benzyl.

Further, the present invention provides a compound of Formula 6 or a salt thereof useful as an intermediate used to prepare the compound of Formula 1:

[Formula 6]

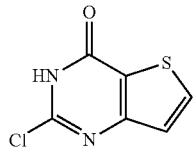

In Formula 6, $R^1$ is $C_{1-10}$ alkyl or benzyl.

The present invention also provides a method for preparing a compound of Formula 3 or a salt thereof, comprising the step of allowing a compound of Formula 4 or a salt thereof to react with a compound of Formula 9 or a salt thereof and an organic acid, preferably in the presence of an organic solvent:

[Formula 3]

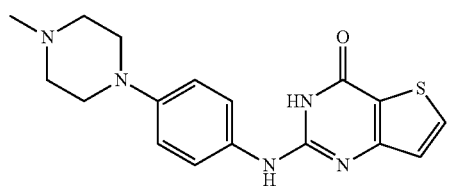

[Formula 4]

[Formula 9]

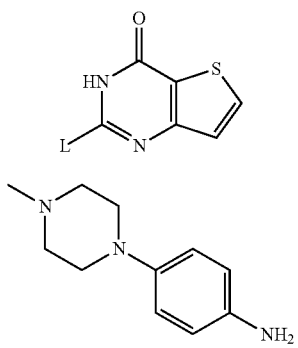

[Formula 4B]

In Formula 4, L is

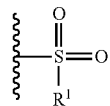

or halogen and $R^1$ is $C_{1-10}$ alkyl or benzyl.

MODE FOR INVENTION

Hereinafter, the present invention will be described in further detail with reference to the following preparative examples. However, it should be understood that the preparative examples are merely provided to aid in understanding the present invention, but not intended to limit the scope of the present invention.

I. Preparation of N-(3-(2-(4-(4-methylpiperazin-1-yl)phenylamino)thieno [2,3-d]pyrimidin-4-yloxy)phenyl)acrylamide (Formula 1)-(1)

EXAMPLE 1

Preparation of 2-(methylsulfonyl)thieno[3,2-d]pyrimidin-4(3H)-one (Formula 4A)

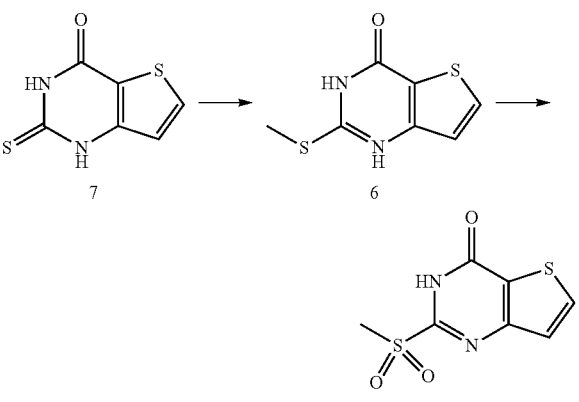

1.1. Preparation of 2-(methylthio)thieno[3,2-d]pyrimidin-4(3H)-one (Formula 6)

90 g (0.49 mol) of 2-thioxo-2,3-dihydrothieno[3,2-d]pyrimidin-4(1H)-one (Formula 7) was dissolved in 900 mL of ethanol, and a solution in which 58.6 g of sodium hydroxide was dissolved in 900 mL of water was added thereto. 32 mL of dimethyl sulfate was added to the reaction mixture at 25° C., and then stirred for 1 hour. After the reaction was completed, the reaction solution was cooled to 5° C., adjusted to pH 2 using 12 N hydrochloric acid at the same temperature, and then stirred at room temperature for 2 hours. The resulting solids were filtered, washed twice with 500 mL of water, and then dried to obtain 93 g (yield: 96%) of the title compound, 2-(methylthio)thieno[3,2-d]pyrimidin-4(3H)-one (Formula 6).

$^1$H-NMR (300 MHz, DMSO-$d_6$) δ 12.77(s, 1H), 8.11 (s, 1H), 7.29 (s, 1H), 3.42 (s, 1H), 2.51 (s, 3H)

1.2. Preparation of 2-(methanesulfonyl)thieno[3,2-d]pyrimidin-4(3H)-one (Formula 4A)

90 g (0.45 mol) of the 2-(methylthio)thieno[3,2-d]pyrimidin-4(3H)-one (Formula 6) obtained in Example 1.1 was dissolved in 1.80 L of ethyl acetate, and 315 g of metachloroperoxybenzoic acid was added thereto at 4° C. and then stirred for 3 hours. After the reaction was completed, the reaction solution was heated to 25° C., and stirred for 12 hours. The resulting solids were filtered to obtain 84 g (yield: 81%) of the title compound, 2-(methanesulfonyl)thieno[3,2-d]pyrimidin-4(3H)-one (Formula 4A).

$^1$H-NMR (300 MHz, DMSO-$d_6$) δ 8.39(d, 1H), 7.61 (d, 1H), 3.45 (s, 3H)

EXAMPLE 2

Preparation of 2-((4-(4-methylpiperazin-1-yl)phenyl)amino) thieno[3,2-d]pyrimidin-4(3H)-one (Formula 3)

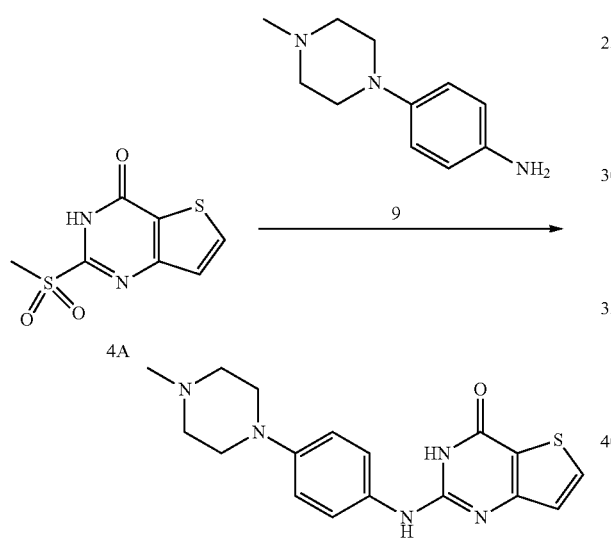

2.1. Preparation by Extraction Method 10 g of the 2-(methanesulfonyl)thieno[3,2-d]pyrimidin-4(3H)-one (Formula 4A) obtained in Example 1.2 was dissolved in 500 mL of acetonitrile, and 10 mL of trifluoroacetic acid and 9 g of 4-(4-methylpiperazin-1-yl)aniline (Formula 9) were added thereto at 25° C. . The resulting mixture was heated under reflux for 1 hour. After the reaction was completed, the reaction solution was neutralized with a saturated and aqueous NaHCO$_3$ solution at room temperature. The reaction solution was extracted with 250 mL of dichloromethane and was distilled under reduced pressure. 10 mL of ethyl acetate was added to resulting residue, which was filtered and dried with warm wind to obtain 12 g (yield: 81%) of the title compound, 2-((4-(4-methylpiperazin-1-yl)phenyl)amino)thieno[3,2-d]pyrimidin-4(3H)-one (Formula 3).

$^1$H-NMR (300 MHz, DMSO-$d_6$) δ 10.89 (s, 1H), 8.51(s, 1H), 8.00 (s, 1H), 7.44 (s, 2H), 7.11 (s, 1H), 6.91 (m, 2H), 3.09 (m, 4H), 2.46 (m, 6H), 2.24 (s, 3H)

2.2. Preparation by Crystallization Method 50 g of the 2-(methanesulfonyl)thieno[3,2-d]pyrimidin-4(3H)-one (Formula 4A) obtained in Example 1.2 was dissolved in 500 mL of acetonitrile, and 50 mL of trifluoroacetic acid and 45 g of 4-(4-methylpiperazin-1-yl)aniline (Formula 9) were added thereto at 25° C. . The resulting mixture was heated under reflux for 1 hour. After the reaction was completed, the reaction solution was neutralized with a saturated and aqueous NaHCO$_3$ solution at room temperature. The resulting solids were filtered, washed with 500 mL of water, dried with warm wind to obtain 70 g (yield: 94%) of the title compound, 2-((4-(4-methylpiperazin-1-yl)phenyl)amino)thieno[3,2-d]pyrimidin-4(3H)-one (Formula 3).

EXAMPLE 3

Preparation of N-(3-(2-(4-(4-methylpiperazin-1-yl) phenyl amino)thieno[2,3-d]pyrimidin-4-yloxy)phenyl)acrylamide (Formula 1)

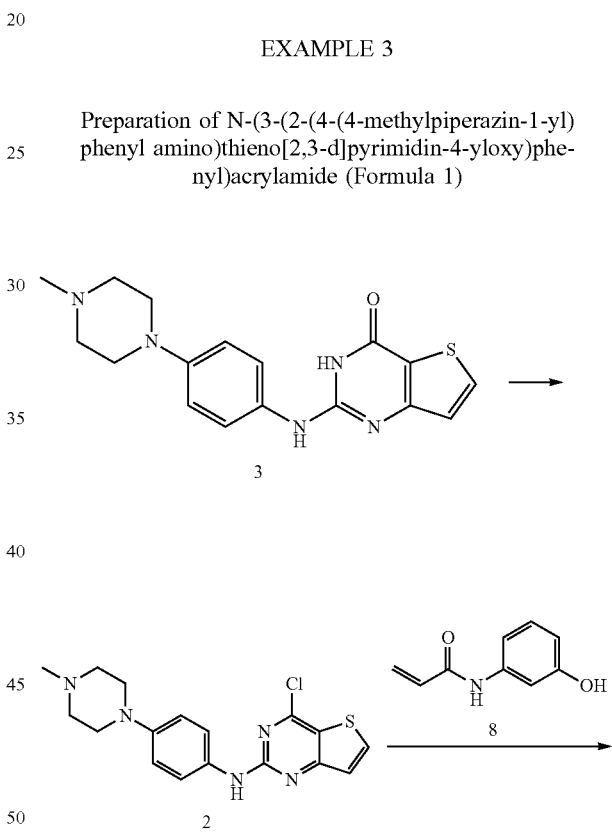

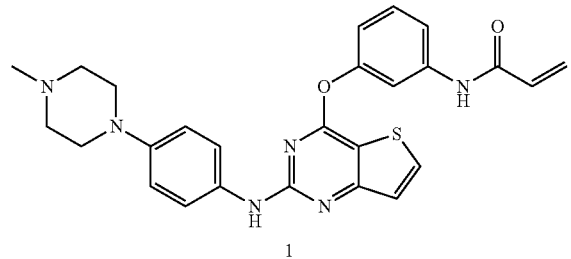

3.1. Preparation of 4-chloro-N-(4-(4-methylpiperazin-1-yl)phenyl)thieno [3,2-d]pyrimidine-2-amine (Formula 2)

After 150 g (0.44 mol) of 2-((4-(4-methylpiperazin-1-yl)phenyl)amino)thieno[3,2-d]pyrimidin-4(3H)-one (Formula 3) obtained in Example 2 was dissolved in 600 mL of acetonitrile, the reaction mixture was heated to 75° C. . 124 mL of phosphorus oxychloride (POCl₃) diluted with 150 mL of acetonitrile was added thereto, and the reaction mixture was stirred at 75° C. for 1 hour. After the reaction was completed, the reaction mixture was cooled to 25° C. , and 1.5 L of cooling water at 0 to 4° C. was slowly added to the reaction solution. Then, while maintaining the reaction temperature at 20° C. or lower, 263 g of sodium hydroxide dissolved in 750 mL of water was added to the reaction solution and the resulting mixture was stirred at 25° C. for 1 hour. The resulting solid was filtered, washed with 1.5 L of water, and dried at 50° C. to obtain 180 g (yield: 114%) of the first crude product of the compound of Formula 2.

180 g of the first crude product was dissolved in 3.0 L of a mixed solvent of dichloromethane and methanol (3:2, volumetric ratio), and the resulting solution was stirred at 25° C. for 1 hour. Then, the stirred solution was filtered through diatomite to remove foreign material, and the filtrate was distilled under reduced pressure. 1.5 L of a mixed solvent of acetone and water (8:2, volumetric ratio) was added to the resulting residue, and the mixture was stirred at 25° C. for 2 hours. The resulting solid was filtered and dried at 50° C. to obtain 125 g (yield: 79%) of the title compound, 4-chloro-N-(4-(4-methylpiperazin-1-yl)phenyl)thieno[3,2-d]pyrimidine-2-amine (Formula 2), as yellow solid.

Melting point: 179 to 181° C.
MS spectrum: m/z=360.11 (M+1)
¹H-NMR(300 MHz, DMSO-d₆) δ 9.74(s, 1H), 8.36(dd, 1H), 7.61(d, 2H), 7.38(dd, 1H), 6.92(d, 2H), 3.06(m, 4H), 2.46(m, 4H), 2.21(s, 3H)

3.2. Preparation of N-(3-(2-(4-(4-methylpiperazin-1-yl)phenylamino)thieno[2,3-d]pyrimidin-4-yloxy)phenyl)acrylamide (Formula 1)

100 g (0.28 mol) of 4-chloro-N-(4-(4-methylpiperazin-1-yl)phenyl)thieno[3,2-d]pyrimidine-2-amine (Formula 2) obtained in Example 3.1 and 54.5 g (0.33 mol) of N-(3-hydroxy)acrylamide (Formula 8) were added to a solution in which 115.2 g (0.83 mol) of potassium carbonate was dissolved in 150 mL of water and 900 mL of acetonitrile was added thereto. The resulting mixture was heated under reflux and stirred for 6 hours. After the reaction was completed, the reaction mixture was cooled to 30° C. or lower, 2.0 L of water was added thereto, and the mixture was stirred at 15 to 20° C. for 15 hours. The resulting solid was filtered, washed with 300 mL of a mixed solvent of acetonitrile and water (1:2, volumetric ratio), and dried to obtain 113 g (yield: 84%) of the title compound of Formula 1, N-(3-(2-(4-(4-methylpiperazin-1-yl)phenylamino) thieno[2,3-d]pyrimidin-4-yloxy)phenyl)acrylamide (Formula 1).

Melting point: 203 to 205° C.
MS spectrum: m/z=487.19 (M+1)
¹H-NMR(300 MHz, DMSO-d₆) δ 10.37(s, 1H), 9.24(s, 1H), 8.27(d, 1H), 7.71(d, 1H), 7.64(d, 1H), 7.49-7.41(m, 3H), 7.32(d, 1H), 7.07(dd, 1H), 6.71(d, 2H), 6.42(dd, 1H), 6.28(dd, 1H), 5.78(dd, 1H), 2.99(t, 4H), 2.43(t, 4H), 2.21(s, 3H)

II. Preparation of N-(3-(2-(4-(4-methylpiperazin-1-yl)phenylamino)thieno [2,3-d]pyrimidin-4-yloxy)phenyl)acrylamide (Formula 1)-(2)

EXAMPLE 4

Preparation of 2-(chloro)thieno[3,2-d]pyrimidin-4(3H)-one (Formula 4B)

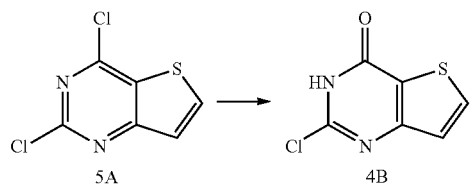 [SMILES: Clc1nc(Cl)c2sccc2n1 ; O=c1[nH]c(Cl)nc2ccsc12]

150 g (0.73 mol) of 2,4-dichlorothieno[3,2-d]pyrimidine (Formula 5A) was dissolved in 1.2 L of a mixed solvent of tetrahydrofuran and water (4:1, volumetric ratio), and a solution in which 70 g of sodium hydroxide was dissolved in 300 mL of water was added thereto. The resulting mixture was heated to 40° C. and then stirred for 4 hours. The reaction solution was cooled to 35° C., and 83.6 mL of acetic acid was added to the reaction solution and then stirred for 2 hours. The resulting solids were filtered, washed with 1.5 L of water, and then dried to obtain 120 g (yield: 89%) of the title compound, 2-(chloro)thieno[3,2-d]pyrimidin-4(3H)-one (Formula 4B).

¹H-NMR (300 MHz, DMSO-d₆) δ 13.53 (brs, 1H), 8.24 (d, 1H), 7.38 (d, 1H)

EXAMPLE 5

Preparation of 2-((4-(4-methylpiperazin-1-yl)phenyl)amino) thieno[3,2-d]pyrimidin-4(3H)-one (Formula 3)

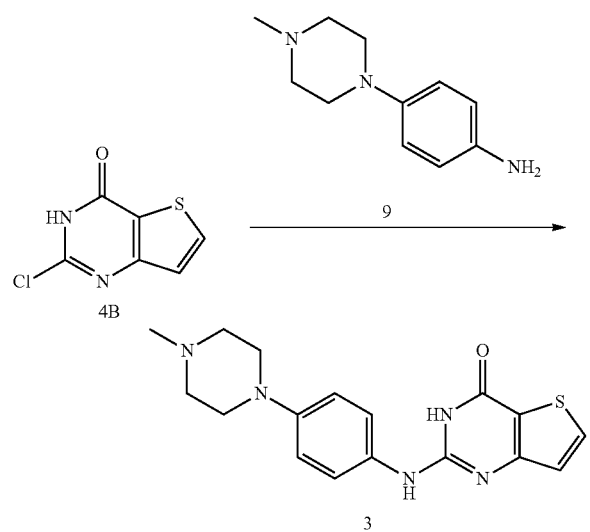

100 g of 2-chlorothieno[3,2-d]pyrimidin-4(3H)-one (Formula 4B) obtained in Example 4 was dissolved in 1 L of ethanol, and 102 g of 4-(4-methylpiperazin-1-yl)aniline (Formula 9) and 92 mL of acetic acid were added thereto at 25° C. The resulting mixture was heated under reflux for 6 hours. After the reaction was completed, 300 mL of triethylamine was added dropwise to the reaction solution at 70° C. . The reaction solution was cooled to 30° C. , and filtered. The resulting residue was washed with 1 L of ethanol, and dried with warm wind to obtain 127 g (yield: 70%) of 2-((4-(4-methylpiperazin-1-yl)phenyl)amino) thieno[3,2-d]pyrimidin-4(3H)-one (Formula 3) of the title compound.

EXAMPLE 6

Preparation of N-(3-(2-(4-(4-methylpiperazin-1-yl) phenyl amino)thieno[2,3-d]pyrimidin-4-yloxy)phenyl)acrylamide (Formula 1)

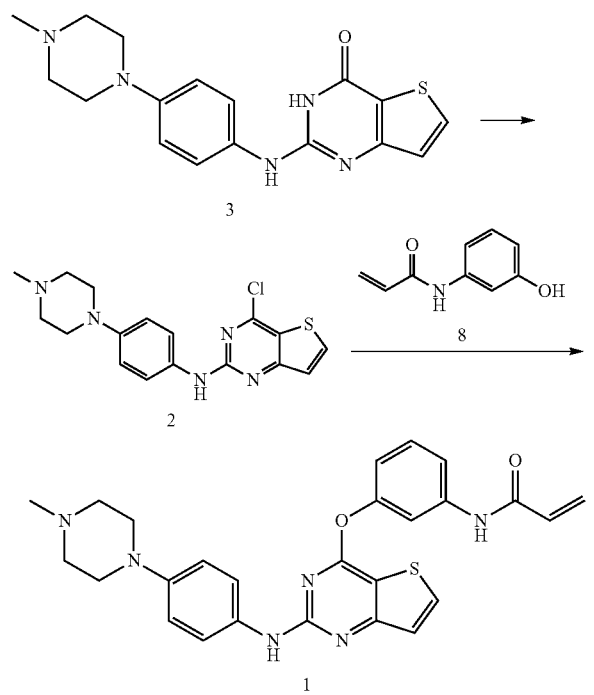

N-(3-(2-(4-(4-methylpiperazin-1-yl)phenyl amino)thieno [2,3-d]pyrimidin-4-yloxy)phenyl)acrylamide (Formula 1) was prepared by employing 2-((4-(4-methylpiperazin-1-yl) phenyl)amino)thieno [3,2-d]pyrimidin-4(3H)-one (Formula 3) obtained in Example 5 according to the same procedure as in Example 3.

The invention claimed is:

1. A compound of the following Formula 2 or a salt thereof:

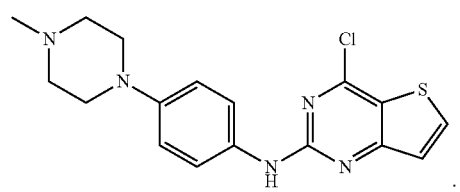

Formula 2

2. A compound of the following Formula 3 or a salt thereof:

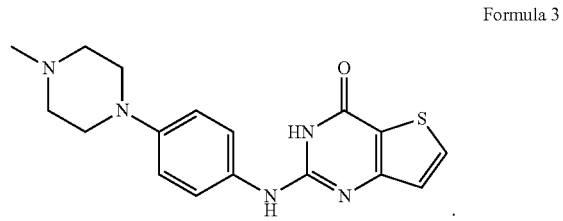 [SMILES: CN1CCN(c2ccc(Nc3nc4ccsc4c(=O)[nH]3)cc2)CC1]

Formula 3

3. A compound of the following Formula 4 or a salt thereof:

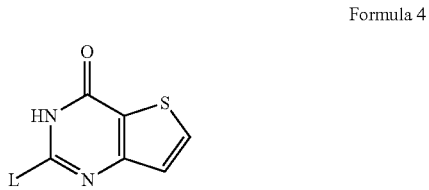

Formula 4 wherein L is

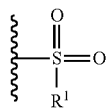

and $R^1$ is $C_{1-10}$ alkyl or benzyl.

4. A method for preparing a compound of the following Formula 3 or a salt thereof, comprising the step of allowing a compound of the following Formula 4 or a salt thereof to react with a compound of the following Formula 9 or a salt thereof and an organic acid:

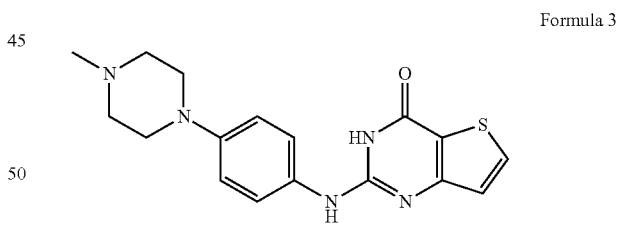

Formula 3

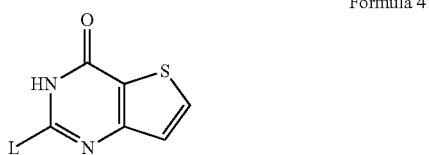

Formula 4

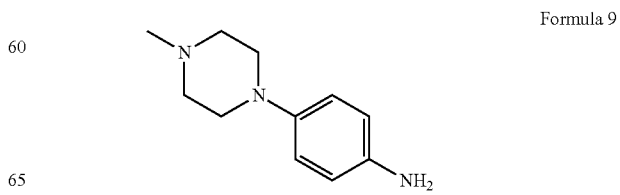

Formula 9 wherein L is
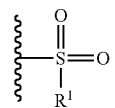
or halogen and $R^1$ is $C_{1-10}$ alkyl or benzyl.
* * * * *